US009662446B2

(12) United States Patent
Fukuda

(10) Patent No.: US 9,662,446 B2
(45) Date of Patent: May 30, 2017

(54) PERICARDIAL-LIQUID LEVEL CONTROL SYSTEM

(71) Applicant: OLYMPUS CORPORATION, Tokyo (JP)

(72) Inventor: Hiroshi Fukuda, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 386 days.

(21) Appl. No.: 14/283,288

(22) Filed: May 21, 2014

(65) Prior Publication Data
US 2014/0257177 A1 Sep. 11, 2014

Related U.S. Application Data

(63) Continuation of application No. PCT/JP2012/081579, filed on Nov. 29, 2012.

(51) Int. Cl.
*A61M 5/00* (2006.01)
*A61M 5/172* (2006.01)
*A61B 1/015* (2006.01)
*A61M 1/00* (2006.01)
*A61M 5/142* (2006.01)
*A61B 5/0456* (2006.01)

(52) U.S. Cl.
CPC ........... *A61M 5/1723* (2013.01); *A61B 1/015* (2013.01); *A61M 1/0084* (2013.01); *A61M 5/142* (2013.01); *A61B 5/0456* (2013.01)

(58) Field of Classification Search
CPC .... A61B 1/015; A61B 5/0456; A61M 1/0084; A61M 5/142; A61M 5/1723
See application file for complete search history.

(56) References Cited

U.S. PATENT DOCUMENTS

| 4,598,697 A | * | 7/1986 | Numazawa | ......... | A61M 1/1086 600/17 |
| 4,991,578 A | | 2/1991 | Cohen | | |

(Continued)

FOREIGN PATENT DOCUMENTS

| JP | 4040672 B2 | 1/2008 |
| WO | WO 2008/134267 A2 | 11/2008 |

OTHER PUBLICATIONS

International Search Report dated Jan. 15, 2013 issued in PCT/JP2012/081579.

(Continued)

*Primary Examiner* — Amanda Patton
(74) *Attorney, Agent, or Firm* — Scully, Scott, Murphy & Presser, P.C.

(57) ABSTRACT

Provided is a pericardial-liquid level control system with which a good viewing field can be ensured for an endoscope image without causing cardiac tamponade. A pericardial-liquid level control system is employed, including a sheath that is inserted into the pericardium; pumps that supply and expel liquid to and from the sheath; electrocardiogram electrodes that detect electrocardiographic information; and a pump control device that, in synchronization with the electrocardiographic information detected by the electrocardiogram electrodes, controls the pumps so that the liquid is supplied to the pericardium via the sheath during contraction of the heart and the liquid is expelled from the pericardium via the sheath during expansion of the heart.

7 Claims, 9 Drawing Sheets

(56) References Cited

U.S. PATENT DOCUMENTS

| | | |
|---|---|---|
| 5,391,199 A | 2/1995 | Ben-Haim |
| 5,533,958 A * | 7/1996 | Wilk ................ A61B 17/00234 600/18 |
| 6,585,635 B1 | 7/2003 | Aldrich |
| 2004/0087831 A1 | 5/2004 | Michels et al. |
| 2005/0273129 A1 | 12/2005 | Michels et al. |
| 2012/0130151 A1 | 5/2012 | Kassab et al. |

OTHER PUBLICATIONS

English abstract only of WO9502995 A1 dated Feb. 2, 1995.
Extended Supplementary European Search Report dated Jun. 25, 2015 from related European Application No. 12 85 6557.9.

* cited by examiner

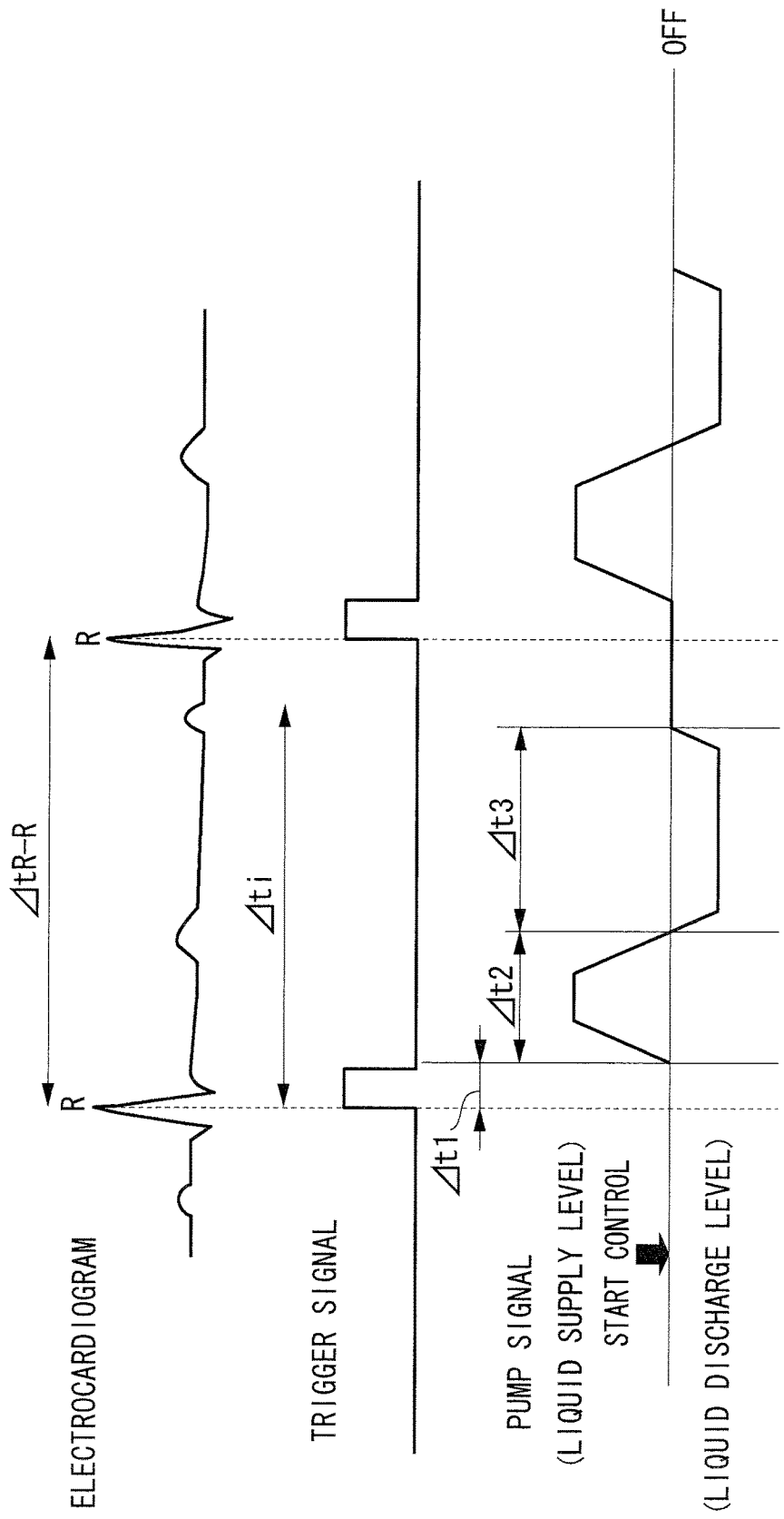

PERICARDIAL-LIQUID LEVEL CONTROL SYSTEM

CROSS-REFERENCE TO RELATED APPLICATIONS

This is a continuation of International Application PCT/JP2012/081579, with an international filing date of Nov. 29, 2012, which is hereby incorporated by reference herein in its entirety. This application claims the benefit of Japanese Patent Application No. 2011-270259, the contents of which are incorporated herein by reference.

TECHNICAL FIELD

The present invention relates to a pericardial-liquid level control system for controlling the amount of liquid in the pericardium.

BACKGROUND ART

In the related art, there is a known technique in which gas such as carbon dioxide or the like is injected into the pericardium in order to ensure a sufficient viewing field for an endoscope image when a device such as an endoscope is inserted into the pericardium and endoscopy or treatment using an instrument is performed in the pericardium (for example, see Patent Literature 1).

CITATION LIST

Patent Literature

{PTL 1} U.S. Patent Application Publication No. 2005/0273129 Specification

SUMMARY OF INVENTION

Technical Problem

Filling the pericardium with gas, as in the technique disclosed in Patent Literature 1, causes the followings.
(1) Tissue gets damaged due to drying of the epicardium.
(2) Ultrasonic waves from an ultrasonic probe disposed on a body surface or at an esophageal wall are reflected by a gas layer, thus impeding propagation of the ultrasonic waves.
(3) Electrodes of an electrode catheter inserted into the pericardium are insulated by the surrounding gas, thus impeding transmission of electrical signals.

On the other hand, when liquid is injected into the pericardium, this causes so-called cardiac tamponade in which pulsing of the heart is impeded by the liquid injected into the pericardium.

The present invention provides a pericardial-liquid level control system with which a good viewing field can be ensured for an endoscope image without causing cardiac tamponade.

Solution to Problem

An aspect of the present invention employs a pericardial-liquid level control system including a pipe that is inserted into a pericardium; a pump that supplies and expels liquid to and from the pipe; an electrocardiographic-information detecting portion that detects electrocardiographic information; and a controlling portion that, in synchronization with the electrocardiographic information detected by the electrocardiographic-information detecting portion, controls the pump so that the liquid is supplied to the pericardium via the pipe during contraction of the heart and the liquid is expelled from the pericardium via the pipe during expansion of the heart.

BRIEF DESCRIPTION OF DRAWINGS

FIG. 11 is a timing chart showing the operation of the pericardial-liquid level control system in FIG. 8.

DESCRIPTION OF EMBODIMENTS

First Embodiment

A pericardial-liquid level control system 101 according to a first embodiment of the present invention will be described below with reference to the drawings.

Figure 1:
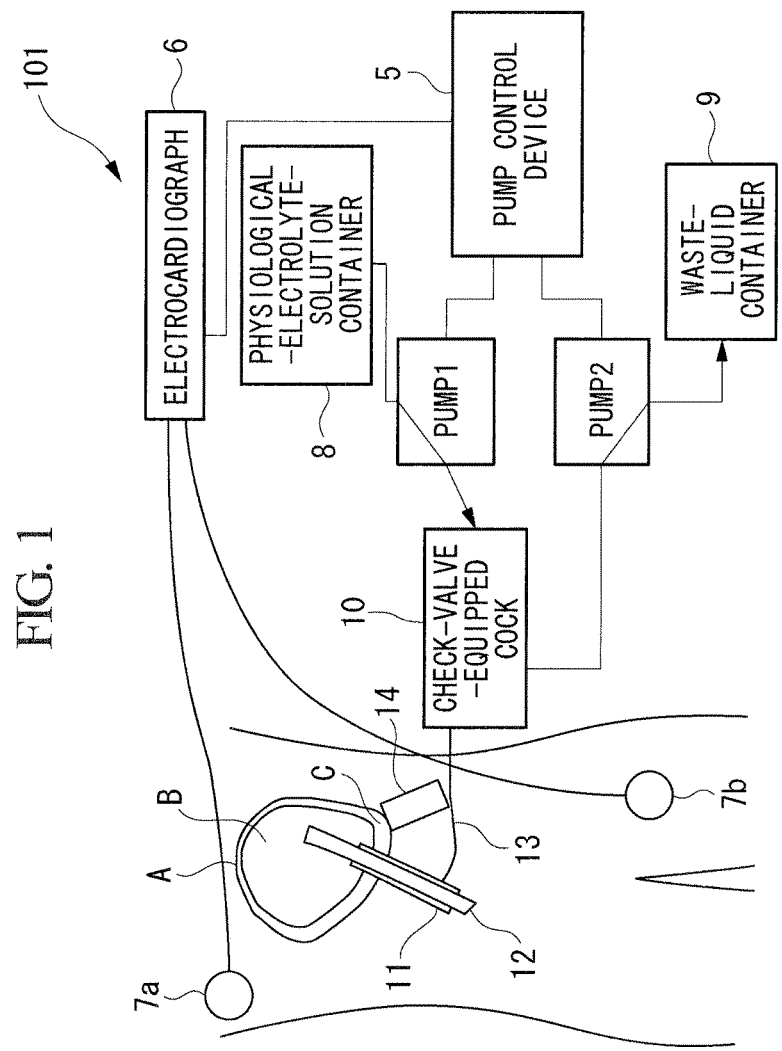
FIG. 1 is a diagram showing, in outline, the configuration of a pericardial-liquid level control system according to a first embodiment of the present invention.

As shown in FIG. 1, the pericardial-liquid level control system 101 in this embodiment is provided with pumps 1 and 2 that transport a certain amount of liquid, a pump control device (controlling portion) 5 that controls these pumps 1 and 2, an electrocardiograph (electrocardiogram generating unit) 6 that sends an electrocardiogram to the pump control device 5, electrocardiogram electrodes (electrocardiographic information detecting portions) 7a and 7b that are attached to the body surface for measuring the electrocardiogram, a physiological-electrolyte-solution container 8 in which physiological saline solution is kept, a waste-liquid container 9 in which liquid expelled from a pericardium C is stored, and a check-valve-equipped cock (flow-channel joining portion) 10 that combines liquid-feeding routes from the pumps 1 and 2 into a single route.

As described later, reference sign 14 indicates an ultrasonic probe for acquiring an ultrasonic image by emitting ultrasonic waves into a heart B from the body surface.

A liquid-feeding route 13 that connects the body exterior with the interior of the pericardium C is a tube, and one end thereof is connected to a gap between the inner space of a sheath (pipe) 11 inserted from below the xiphoid process and a device (an endoscope 12 in this case) inserted into the sheath 11. In addition, the other end of the liquid-feeding route 13 that connects the body exterior with the interior of the pericardium C is connected to the check-valve-equipped cock 10.

The sheath 11 is preferably a sheath 11 equipped with a steering mechanism as with, for example, the Agilis steerable sheath 11 made by St. Jude Medical Co. Ltd., and, similar to a general sheath 11, a route (space) thereof that penetrates into the pericardium C is provided with a three-way stop cock (not shown) at the end thereof.

Figure 2:
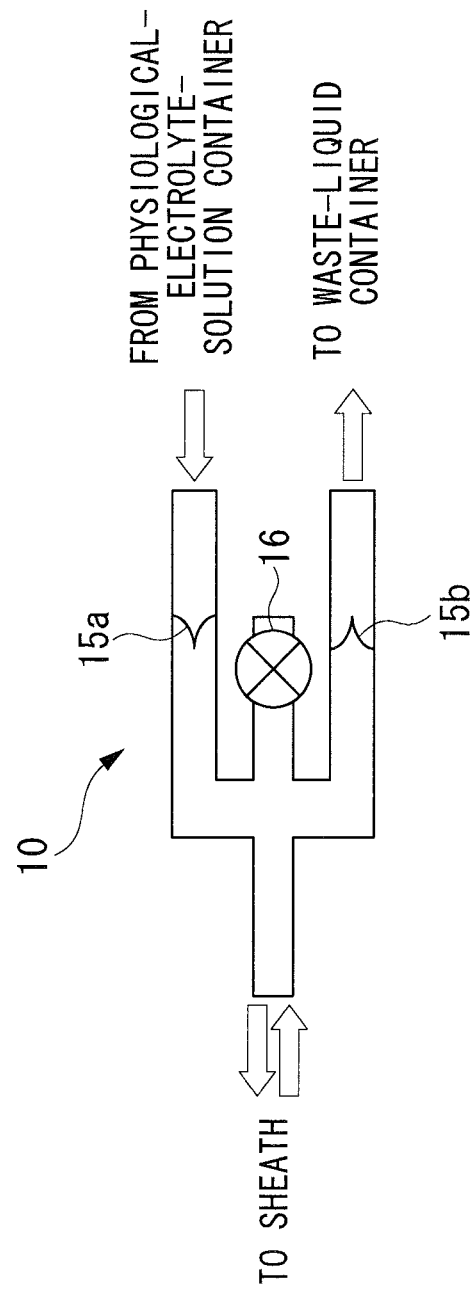
FIG. 2 is an enlarged view of a check-valve-equipped cock in FIG. 1.

The check-valve-equipped (branched) cock 10, such as one shown in FIG. 2, is connected to the three-way stop cock of the sheath 11. The check-valve-equipped cock 10 branches a single flow channel from the sheath 11; one of the branched flow channels is provided with a check valve 15a that only accepts a flow to be injected towards the sheath 11 side, and the other flow channel is provided with a check valve 15b that only accepts a flow from the sheath 11 side.

In the example shown in FIG. 2, although the flow channel is branched into three, and the remaining one is provided with an emergency valve 16 which is released in the case of an emergency in this example, the emergency valve 16 may be substituted by the three-way stop cock of the sheath 11.

In addition, although the check valves 15a and 15b are provided for the purpose of preventing a reverse flow from the waste-liquid container 9, they need not be provided if a type of pump with which a reverse flow is less likely to occur, such as a peristaltic pump or the like, is employed as the pumps 1 and 2.

The electrocardiogram electrodes 7a and 7b are electrodes attached to body surfaces for measuring an electrocardiogram (electrocardiographic information) and output the measured electrocardiographic information to the electrocardiograph 6.

The electrocardiograph 6 generates an electrocardiogram from the electrocardiographic information measured by the electrocardiogram electrodes 7a and 7b and outputs the electrocardiogram to the pump control device 5.

The physiological-electrolyte-solution container 8 is a container in which physiological saline solution is retained. The physiological-electrolyte-solution container 8 is connected to the pump 1, and, by operating the pump 1, the physiological saline solution retained in the physiological-electrolyte-solution container 8 is injected into the pericardium C via the check-valve-equipped cock 10 and the liquid-feeding route 13.

Liquid to be injected into the pericardium C, which is a space between a pericardial membrane A and the heart B, is preferably physiological electrolyte solution, such as a physiological saline solution, Ringer's solution, and so forth, and this embodiment will be described by using physiological saline solution which is physiological electrolyte solution.

The waste-liquid container 9 is a container in which liquid expelled from the pericardium C is stored. The waste-liquid container 9 is connected to the pump 2, and, by operating the pump 2, the physiological saline solution retained in the pericardium C is expelled from the pericardium C via the check-valve-equipped cock 10 and the liquid-feeding route 13 and is transferred to the waste-liquid container 9.

Figure 4:
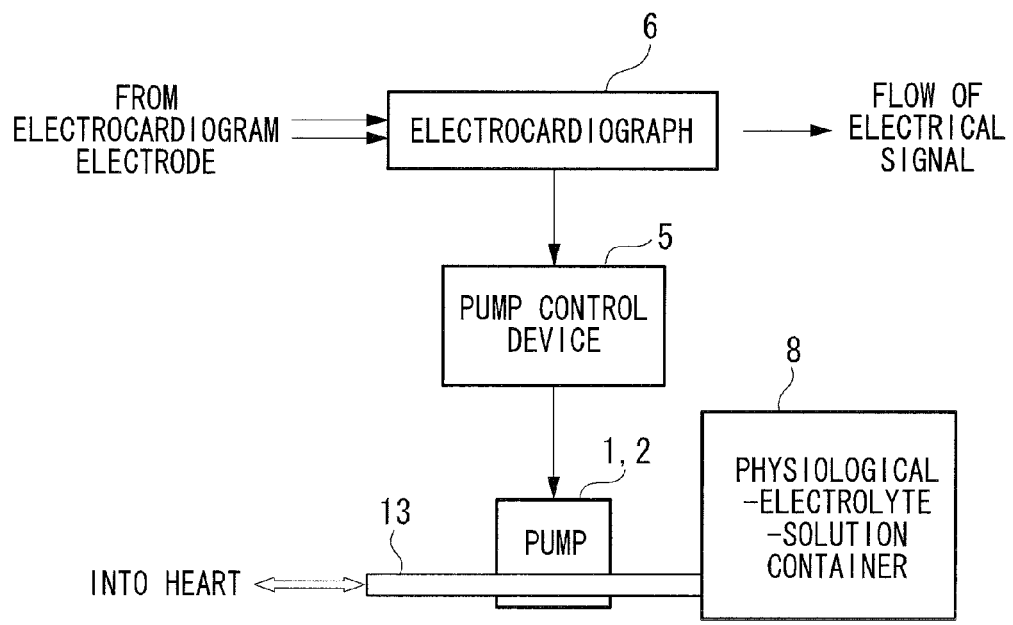
FIG. 4 is a block diagram showing the flow of signals between individual components in FIG. 1.

As shown in FIG. 4, the pump control device 5 controls the pumps 1 and 2 in synchronization with the electrocardiogram (the electrocardiographic information measured by the electrocardiogram electrodes 7a and 7b) generated by the electrocardiograph 6. Specifically, the pump control device 5 operates the pump 1 when the heart B contracts, to supply the physiological saline solution to the pericardium C via the liquid-feeding route 13. On the other hand, the pump control device 5 operates the pump 2 when the heart B expands, to expel the liquid from the pericardium C via the liquid-feeding route 13.

Figure 5:
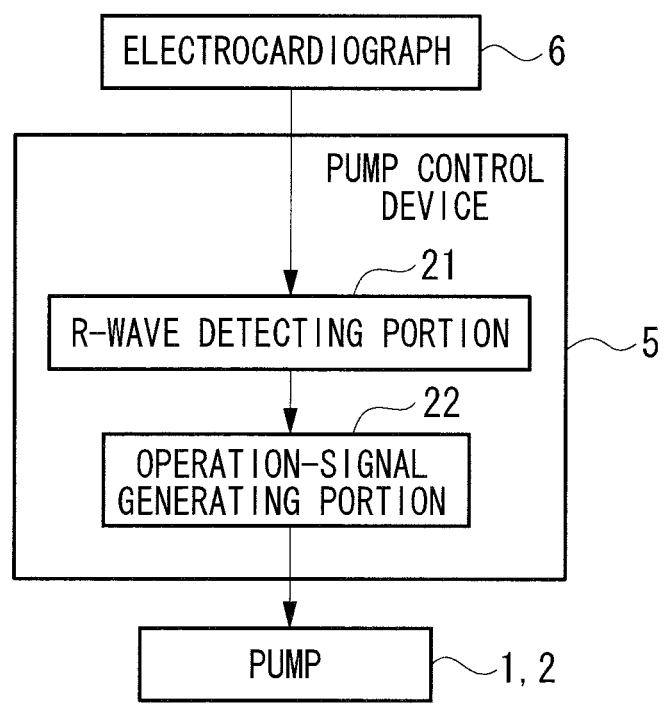
FIG. 5 is a functional block diagram of a pump control device in FIG. 1.

As shown in FIG. 5, as its functions, the pump control device 5 is provided with an R-wave detecting portion 21 that receives signals from the electrocardiograph 6 and detects R-waves from the electrocardiogram and an operation-signal generating unit 22 that outputs, to the pumps 1 and 2, an injection operation signal for injecting liquid into the pericardium C from the physiological-electrolyte-solution container 8 and a suction operation signal for sucking the liquid from the pericardium C into the waste-liquid container 9 after a predetermined period of time since the time of the R wave detection.

Here, cardiac tamponade is caused by a drop in the cardiac output which is caused by entering the systolic phase without a sufficient expansion of the ventricles due to the liquid in the pericardium C impeding the expansion of the ventricles during the diastolic phase when an excessive amount of liquid is retained in the pericardium C. In other words, if the amount of liquid in the pericardium C is controlled so that the ventricles can sufficiently be expanded at the end of the diastole, the occurrence of cardiac tamponade can be reduced.

Figure 3:
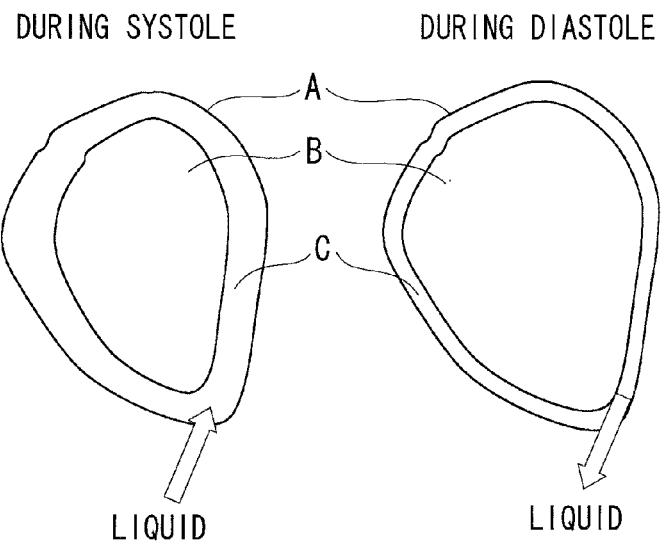
FIG. 3 is a diagram showing contracted and expanded states of the heart.

Therefore, with the pericardial-liquid level control system 101 according to this embodiment, as shown in FIG. 3, liquid is injected into the pericardium C during the systole, and the liquid is sucked out of the pericardium C during the diastole in synchronization with the electrocardiogram.

By doing so, because the amount of liquid in the pericardium C at the end of the diastole can be reduced to an amount with which the heart B can sufficiently be expanded at the end of the diastole, the liquid can be retained in the pericardium C without causing cardiac tamponade. In addition, by retaining the liquid in the pericardium C, drying of the epicardium can be prevented, and a sufficient viewing field can also be ensured for an endoscope inserted into the pericardium C by expanding the interior of the pericardium C. Furthermore, it is possible to simultaneously perform ultrasonic observation via the body surface and the esophageal wall, electrode-position detection based on the electrical impedance of the endoscope 12 inserted into the pericardium C, and so forth.

In addition, it is not only possible to utilize the liquid retained in the pericardium C as an acoustic medium for an ultrasonic endoscope 12 inserted into the pericardium C or a cooling medium for an ablation endoscope 12 inserted into the pericardium C, but it is also possible to lift the heart B in the pericardium C with a low force due to the buoyancy of the liquid in the pericardium C, and thus the back wall of the heart B can be more easily accessed.

A method of using the pericardial-liquid level control system 101 according to this embodiment will be described below.

First, by using the method of Sosa et al. (reference: Sosa E. et al. Nonsurgical transthoracic epicardial catheter ablation to treat recurrent ventricular tachycardia occurring late after myocardial infarction. J. Am. Coll. Cardiol. 2000. 35: 1442-1449), the sheath 11 (for example, the Agilis steerable sheath 11 made by St. Jude Medical Co. Ltd.) is indwelt in the pericardium C from below the xiphoid process in the state in which the interior of the sheath 11 is filled with the physiological saline solution.

Next, in order to ensure a sufficient viewing field for a surface observation of the heart B by means of the endoscope 12, the pump 1 is operated while monitoring the hemodynamics of a patient to inject the physiological electrolyte solution into the pericardium C from the physiological-electrolyte-solution container 8 via the check-valve-equipped cock 10 and a gap between the endoscope 12 and the sheath 11.

At this time, by starting to control the amount of physiological electrolyte solution, described later, at the pump control device 5 to which a signal line from the electrocardiograph 6 is connected, the physiological electrolyte solution is injected into the pericardium C by means of the pump 1 during the ventricular systolic phase. In addition, the pump 2 is operated so as to correspond to the subsequent ventricular diastolic phase, and thus, excess liquid in the pericardium C which causes a failure in the hemodynamics is expelled to the waste-liquid container 9 from the pericardium C.

Figure 6:
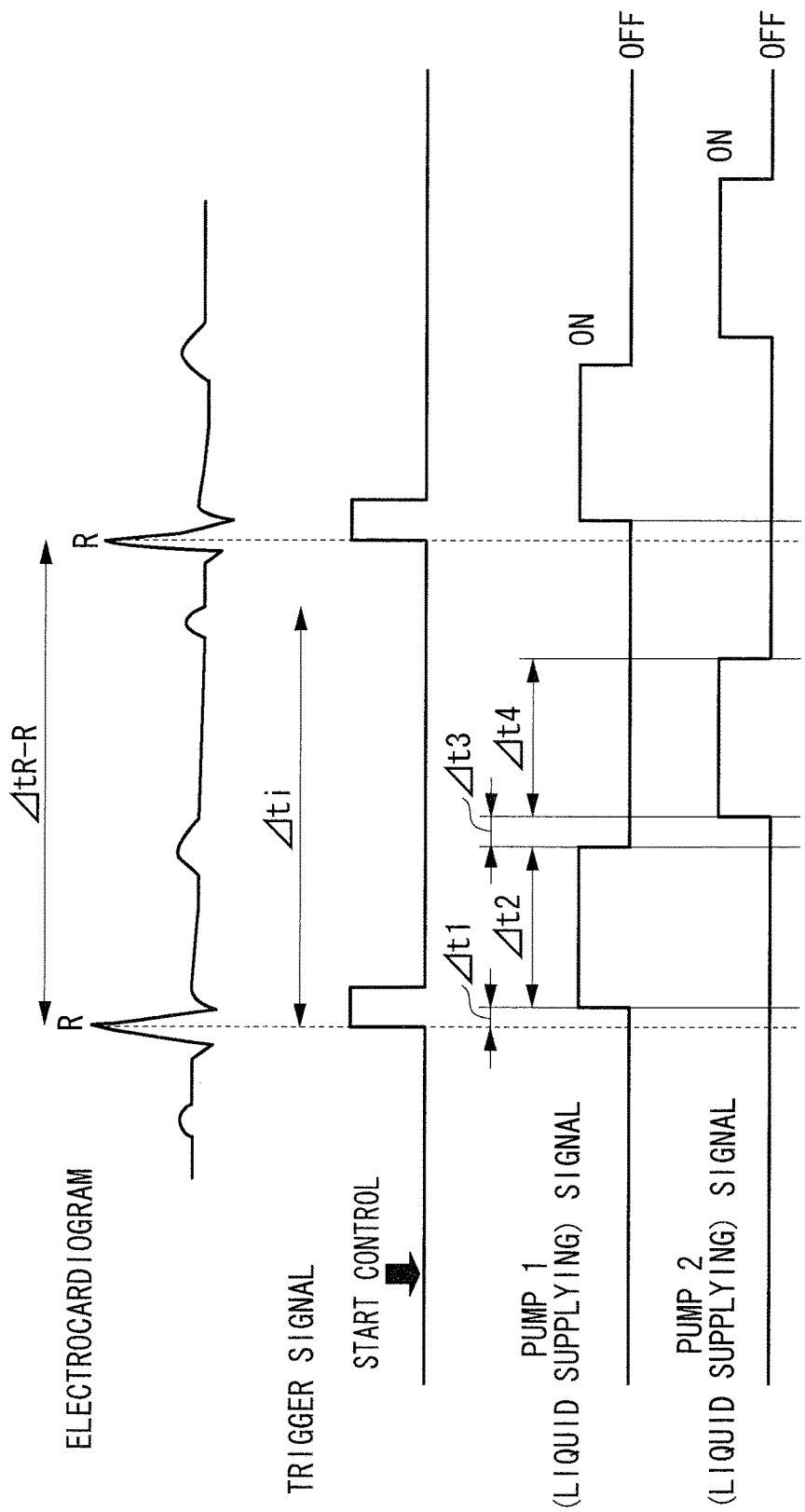
FIG. 6 is a timing chart showing the operation of the pericardial-liquid level control system in FIG. 1.

FIG. 6 shows an example of the control of the amount of physiological electrolyte solution (control of the pumps 1 and 2 for injecting and expelling the physiological electrolyte solution) by the pump control device 5.

A trigger signal is generated under a trigger condition for capturing R-waves from the electrocardiogram, and a signal for operating the pump 1 that injects the physiological electrolyte solution into the pericardium C for a certain period of time $\Delta t2$ after a certain period of time ($\Delta t1$) from the initiation of the trigger signal is output to the pump 1.

In addition, after a time interval $\Delta t3$ from when the operating signal for the pump 1 is turned off, a signal for operating the pump 2 that expels the physiological electrolyte solution from the pericardium C for a certain period of time $\Delta t4$ is output to the pump 2.

Here, it is necessary to select the respective operating time so as to satisfy the relationship below:

$$RR \text{ interval}(\Delta t_{R-R}) > \Delta t1 + \Delta t2 + \Delta t3 + \Delta t4.$$

With the pericardial-liquid level control system 101 according to this embodiment, the amount of liquid in the pericardium C can be stably controlled even if the RR interval (heart-beat movement interval) fluctuates within a range in which the above relationship is satisfied. Therefore, by determining non-response time $\Delta ti$ from the output of one trigger signal to the output of the next trigger signal in the following manner, a trigger-signal output due to noise can be reduced, and the amount of physiological saline solution can be stably controlled:

$$\Delta t1 + \Delta t2 + \Delta t3 + \Delta t4 < \Delta ti < \Delta t_{R-R}.$$

Subsequently, control is performed so that the amount of physiological saline solution injected from the physiological-electrolyte-solution container 8 during the time $\Delta t2$ by means of the pump 1 and the amount of liquid expelled to the waste-liquid container during the time $\Delta t4$ by means of the pump 2 become equal. Although a case in which $\Delta t2$ is set to be equal to $\Delta t4$ by making the liquid supplying speed and the liquid discharging speed equal is described as an example here, naturally, there is no limitation thereto, and the liquid feeding/discharging speed and the liquid feeding/discharging time may be adjusted so that the liquid supply level and the liquid discharge level become the same.

As described above, with the pericardial-liquid level control system 101 according to this embodiment, by increasing the amount of liquid in the pericardium C during the systolic phase, a sufficient space can be ensured in the pericardium C for performing observation by means of the endoscope 12 or treatment by using an instrument, fogging of a lens in the endoscope 12 inserted into the pericardium C can also be eliminated, and thus, an endoscope image can be enhanced. In this case, by decreasing the amount of liquid in the pericardium C during the diastolic phase, the effect of the liquid in the pericardium C on the ventricular diastole can be reduced so as not to cause cardiac tamponade.

In addition, damage on the surface of the heart B due to drying of the epicardium can be reduced, and at the same time, an ultrasonic image can be acquired by emitting ultrasonic waves into the heart B from the body surface by means of the ultrasonic probe 14.

Although a case in which the ultrasonic probe 14 is placed on the body surface is illustrated in the example shown in FIG. 1, with the pericardial-liquid level control system 101 according to this embodiment, there is an advantage in that, also with a transesophageal probe or an ultrasonic probe inserted into the pericardium C, an ultrasonic image can be displayed without requiring a special holding mechanism for an acoustic medium.

Furthermore, because buoyancy acts on the heart B by retaining the physiological electrolyte solution, such as physiological saline solution or the like, in the pericardium C, the heart B can be moved in position in the pericardium C even with a weaker force as compared with a case in which gas, such as carbon dioxide or the like, is retained therein. In particular, when treatment is performed by inserting the endoscope 12 at the back wall of the heart B, a sufficient work space can be easily ensured by lifting the heart B. In addition, the liquid in the pericardium C can act as a medium for manipulating the endoscope 12 by utilizing the buoyancy of the liquid.

Second Embodiment

A pericardial-liquid level control system 102 according to a second embodiment will be described with reference to FIG. 7. Hereinafter, for pericardial-liquid level control systems according to individual embodiments, the same reference signs will be assigned to commonalities with the pericardial-liquid level control system according to the embodiment described above, omitting descriptions thereof, and differences from the pericardial-liquid level control system according to the embodiment described above will mainly be described.

Figure 7:
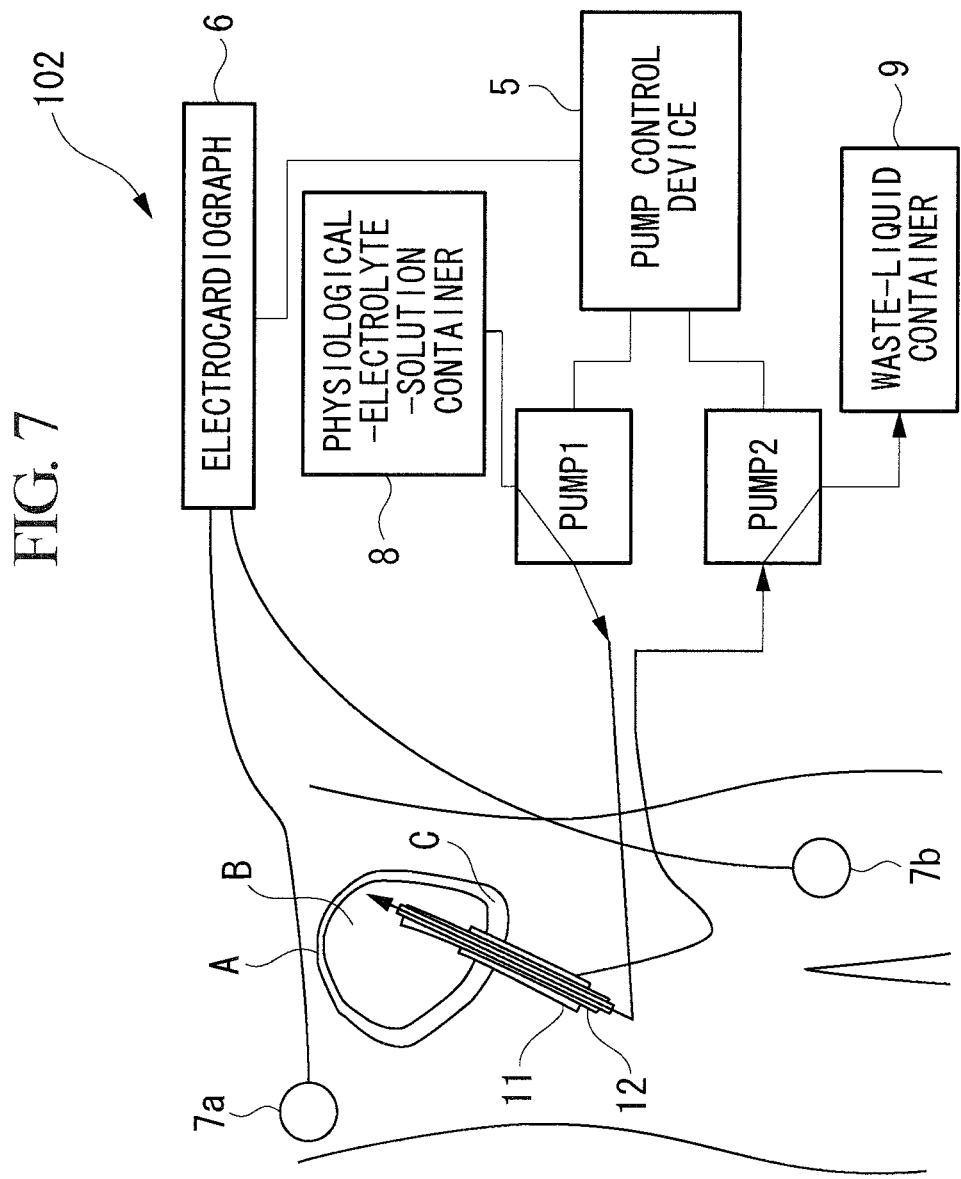
FIG. 7 is a diagram showing, in outline, the configuration of a pericardial-liquid level control system according to a second embodiment of the present invention.

FIG. 7 is a diagram showing, in outline, the configuration of the pericardial-liquid level control system 102 according to this embodiment.

The pericardial-liquid level control system 102 according to this embodiment differs from the pericardial-liquid level control system 101 according to the first embodiment in that an injection pathway into the pericardium C for physiological saline solution and a suction pathway from the pericardium C for the physiological saline solution are provided independently of each other.

The three-way stop cock of the sheath 11 is connected to the pump 2 that discards the liquid in the pericardium C into the waste-liquid container 9 by means of suction, and the pump 1 that injects physiological saline solution into the pericardium C is connected to an unillustrated endoscope through-hole (channel) that is provided as an opening at the tip of the endoscope 12 so as to communicate with the interior of the endoscope 12 inserted into the sheath 11.

With the pericardial-liquid level control system 102 according to this embodiment, because fresh physiological saline solution is supplied to the vicinity of the tip of the endoscope 12, in addition to the same effects as the first embodiment, a high clearness can be maintained for the physiological saline solution in the pericardium C and a clear image can be acquired by means of the endoscope 12.

Third Embodiment

A pericardial-liquid level control system 103 according to a third embodiment will be described with reference to FIGS. 8 to 11.

Figure 8:
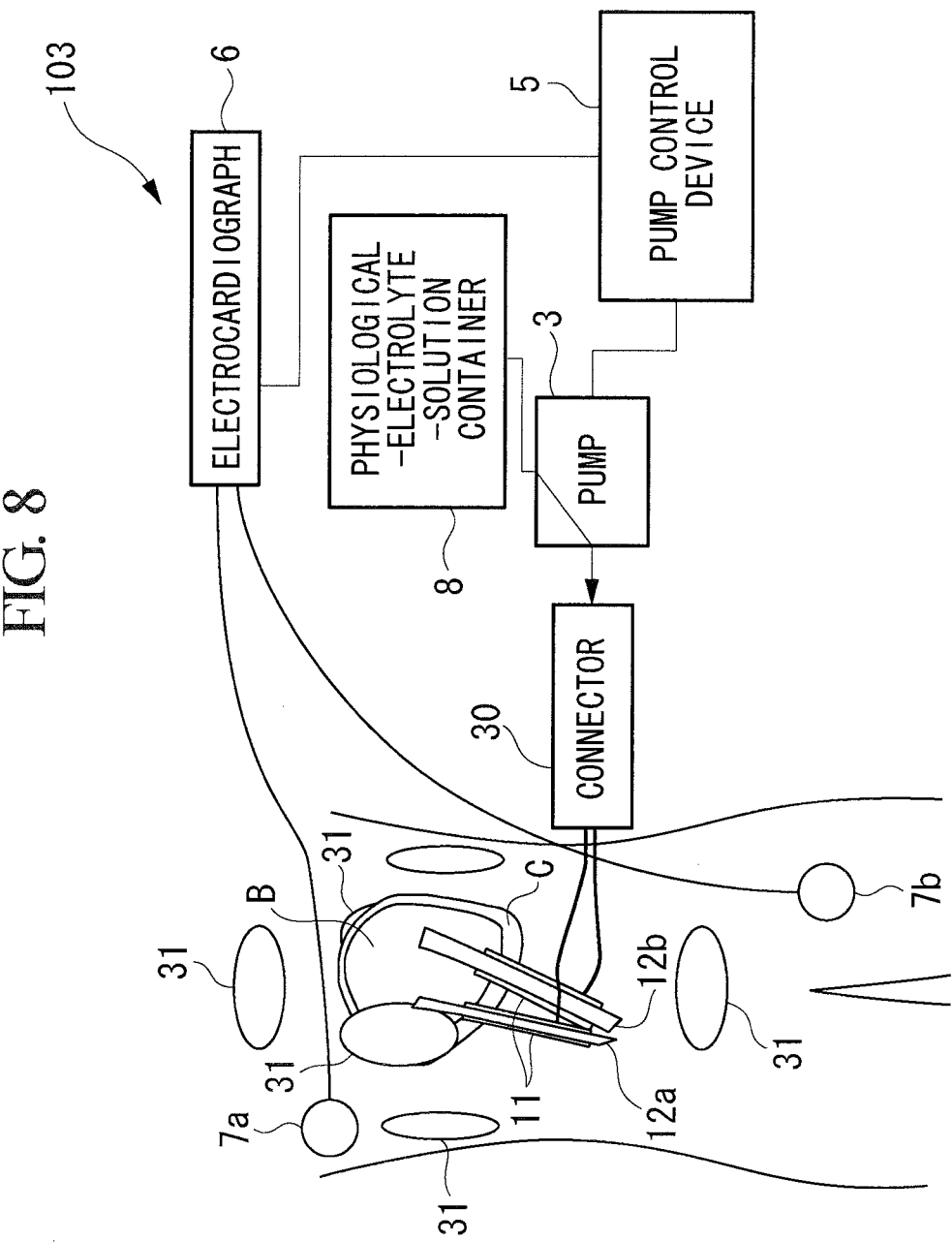
FIG. 8 is a diagram showing, in outline, the configuration of a pericardial-liquid level control system according to a third embodiment of the present invention.

FIG. 8 is a diagram showing, in outline, the configuration of the pericardial-liquid level control system 103 according to this embodiment.

In this embodiment, an example will be described in which a position detection system for the endoscope 12 based on electric impedance is employed in the pericardial-liquid level control system 101 according to the embodiment described above. Here, a case in which, for example, the position detection function of the EnSite NavX system made by St. Jude Medical Co. Ltd. is employed as an endoscope-position detection system based on electrical impedance will be described as an example.

With the EnSite NavX system made by St. Jude Medical Co. Ltd., in order to establish a three-axis electrical potential gradient in a biological subject, pairs of patch electrodes 31 are individually attached to body surfaces at the top and bottom, the front and rear, and the left and right, as shown in FIG. 8; the electrical potential gradient is formed in the biological subject by generating weak current flows between each pair of patch electrodes 31; and position detection is performed based on the electrical potential recorded by electrodes provided in the endoscopes 12 (12a and 12b) inserted into the biological subject.

With this type of endoscope-position detection system based on electrical impedance, there has been a problem in that position detection is difficult for the endoscope 12 inserted into the pericardium C in a state in which the surroundings of the endoscope 12 inserted into the pericardium C are filled with gas.

In this embodiment, an example will be described in which physiological electrolyte solution whose electrical conductivity is close to that of biological tissue is retained in the pericardium C, and position detection of the endoscope 12 is performed based on electrical impedance.

A known liquid, such as physiological saline solution, Ringer's solution, and so forth, can be used as the physiological electrolyte solution used in this embodiment.

In addition, a pump 3 which can be operated in forward/reverse directions is employed in this embodiment instead of the pumps 1 and 2 in the embodiment described above.

First, two sheaths 11 (for example, the Agilis steerable sheaths 11 made by St. Jude Medical Co. Ltd.) are indwelt in the pericardium C by accessing it from below the xiphoid process by using the method of Sosa et al. described above, and, subsequently, an endoscope 12a for observing the interior of the pericardium C and an endoscope 12b such as an ablation catheter or the like are individually inserted into the pericardium C via the sheaths 11.

Figure 9:
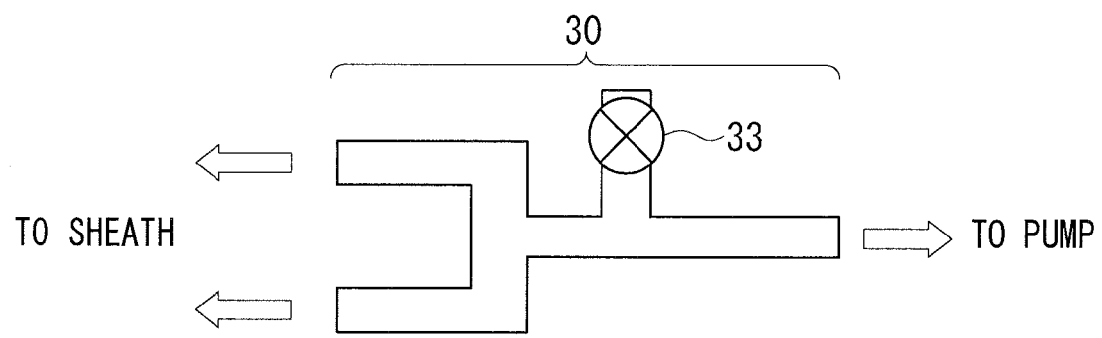
FIG. 9 is an enlarged view of a connector in FIG. 8.

Routes (spaces) for the above-described two sheaths 11 that penetrate into the pericardium C are combined into a single liquid-feeding pathway at ends thereof on the stopcock side of the respective three-way stop cocks (not shown) by means of a connector (flow-channel joining portion) 30 shown in FIG. 9. The combined liquid-feeding pathway is connected to the physiological-electrolyte-solution container 8, in which the physiological electrolyte solution is temporarily stored, and the pump 3.

The connector 30 is provided with a valve 33 that is opened at the time of an emergency and is also used as a pathway for replenishing the physiological electrolyte solution in the pericardium C by means of a syringe or the like via this valve 33.

By combining the plurality of liquid-feeding pathways leading into the pericardium C by the connector 30, even in the case in which the liquid-feeding resistance is different for the individual liquid-feeding pathways from the pericardium C, because adjustments are made so that a large amount of physiological electrolyte solution flows in a liquid-feeding pathway having a low liquid-feeding resistance, whereas only a small amount of physiological electrolyte solution flows in a liquid-feeding pathway having a large liquid-feeding resistance, efficient liquid feeding is possible.

Figure 10:
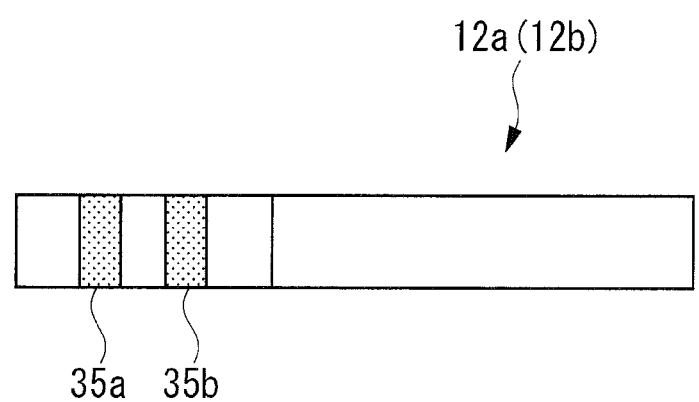
FIG. 10 is a partial enlarged view of a tip of an endoscope in FIG. 8.

As shown in FIG. 10, devices (the endoscopes 12a and 12b in this case) whose positions in the pericardium C need to be detected are provided with, for detecting the positions thereof, a pair of ring electrodes 35a and 35b, such as those provided in catheters for an electrophysiological examination.

The endoscopes 12a and 12b provided with the above-described ring electrodes 35a and 35b are inserted into the pericardium C via the sheaths 11.

The pump control device 5 controls injection/discharge of the physiological electrolyte solution by means of the pump 3. An example of this control is shown in FIG. 11.

At the pump control device 5, a trigger signal is generated under a trigger condition for capturing R-waves in the electrocardiogram, and a signal for injecting the physiological electrolyte solution into the pericardium C is output to the pump 3 after a certain period of time ($\Delta t1$) from the initiation of the trigger signal. At this time, for a time period $\Delta t2$, the signal is output while changing the liquid-feeding speed at the time of starting the injection and ending the injection, as shown by sloping portions of a graph of the liquid supply level/liquid discharge level versus time, shown in FIG. 11. Subsequently, for a time period $\Delta t3$, a signal for expelling the physiological electrolyte solution from the pericardium C is output to the pump 3 so that the pump 3 is operated while changing the discharging speed at the time of starting the discharge and ending the discharging, as with the case of injection.

Here, it is necessary to select the respective operating times so as to satisfy the relationship below:

$$RR\ \text{interval}(\Delta t_{R\text{-}R}) > \Delta t1 + \Delta t2 + \Delta t3.$$

With the pericardial-liquid level control system 103 according to this embodiment, the amount of physiological electrolyte solution in the pericardium C can be stably controlled even if the RR interval (heart-beat movement interval) fluctuates within a range in which the above relationship is satisfied.

As with the first embodiment, also by determining non-response time $\Delta t_i$ as below, a trigger-signal output due to noise can be reduced and the amount of physiological electrolyte solution can be stably controlled:

$$\Delta t1 + \Delta t2 + \Delta t3 < \Delta ti < \Delta t_{R\text{-}R}.$$

Here, by performing control so that the amount of physiological electrolyte solution supplied from the physiological-electrolyte-solution container by means of the pump 3 for the time period $\Delta t2$ and the amount of physiological electrolyte solution discharged over the time period $\Delta t3$ become equal, because there is no increase or decrease in the amount of physiological electrolyte solution in the pericardium C between heart beats, the amount of physiological electrolyte solution in the pericardium C can be stably controlled for an extended period of time.

In addition, because the liquid supplying/discharging speed is gradually changed, as compared with the on-off control described in the first embodiment, the liquid supplying/discharging resistance can be reduced at the time of starting up and shutting down, especially when switching between liquid supply and discharge, and thus, accurate liquid supply/discharge control is possible.

The physiological electrolyte solution may be added to the pericardium C via the valve 33 of the connector 30 shown in FIG. 9 by means of a syringe or the like in the state in which the control of the amount of physiological electrolyte solution in the pericardium C is performed as described above, and the amount of physiological electrolyte solution to be supplied and the amount of physiological electrolyte solution to be discharged are controlled to be equal in accordance with the heart beat by means of the pump 3. By doing so, the total amount of physiological electrolyte solution in the pericardium C can be adjusted while reducing the effects of the amount of physiological electrolyte solution in the pericardium C associated with the heart-beat movement.

In this embodiment, although descriptions have been given about a method in which the pump control device 5 controls the amount of physiological electrolyte solution in the pericardium C so that the liquid supply level and the liquid discharge level of the physiological electrolyte solution during heart beats are controlled to be equal, and the total amount of physiological electrolyte solution in the pericardium C is adjusted by the physiological electrolyte solution injected thereinto from the valve 33 of the connector 30, the adjustment may be made by performing control so that "the liquid supply level of the physiological electrolyte solution>the liquid discharge level of the physiological electrolyte solution" is achieved during heart beats when the total amount of physiological electrolyte solution in the pericardium C needs to be increased and so that "the liquid supply level of the physiological electrolyte solution<the liquid discharge level of the physiological electrolyte solution" is achieved during heat beats when the total amount of physiological electrolyte solution in the pericardium C needs to be reduced.

In addition, although an example was described in this embodiment in which the amount of physiological electrolyte solution is controlled by using gaps between the two sheaths 11 and the individual endoscopes 12a and 12b inserted thereinto as pathways to do so, the number of sheaths 11 is not limited to two, and a greater number of sheaths 11 may be combined into a single liquid supply/discharge pathway, or, in the case in which the endoscope 12 that is inserted into the sheath 11 is provided with liquid feeding/discharging pathways, those liquid feeding/discharging pathways may also be combined.

Furthermore, although an example is shown in FIG. 8 in which electrocardiogram electrodes 7a and 7b attached to the patient are connected to the electrocardiograph and the measured electrocardiogram is input to the pump control device 5, the signals measured between the patch electrodes 31 for forming the graduated electrical potential for position detection may be used as substitutes for the electrocardiogram.

Although the individual embodiments of the present invention have been described in detail with reference to the drawings, specific configurations are not limited to these embodiments, and design alterations are also encompassed within a range that does not depart from the spirit of the present invention. For example, the present invention may be employed in an embodiment in which the individual embodiments described above are appropriately combined.

According to the above embodiments, following aspects can be introduced.

An aspect of the present invention employs a pericardial-liquid level control system including a pipe that is inserted into a pericardium; a pump that supplies and expels liquid to and from the pipe; an electrocardiographic-information detecting portion that detects electrocardiographic information; and a controlling portion that, in synchronization with the electrocardiographic information detected by the electrocardiographic-information detecting portion, controls the pump so that the liquid is supplied to the pericardium via the pipe during contraction of the heart and the liquid is expelled from the pericardium via the pipe during expansion of the heart.

With the aspect of the invention, in the state in which the pipe is inserted into the pericardium, the electrocardiographic information is detected by the electrocardiographic-information detecting portion, and the operation of the pump is controlled by the controlling portion in synchronization with the electrocardiographic information. Specifically, the pump is controlled so that the liquid is supplied into the pericardium via the pipe during contraction of the heart and the liquid is expelled from the pericardium via the pipe during expansion of the heart.

By injecting/expelling the liquid into and from the pericardium in synchronization with the electrocardiographic information as described above, the heart can sufficiently be expanded during expansion of the heart while retaining the liquid in the pericardium by removing the liquid in the pericardium that reduces the expansion of the heart. By doing so, it is possible to prevent so-called cardiac tamponade in which the pulsing of the heart is impeded by the liquid retained in the pericardium.

In addition, by retaining the liquid in the pericardium, drying of the epicardium can be prevented and a sufficient viewing field can also be ensured for an endoscope inserted into the pericardium by expanding the interior of the pericardium by means of the liquid. In addition, the liquid retained in the pericardium can also be utilized as an acoustic medium for an ultrasonic device inserted into the pericardium or as a cooling medium for an ablation device inserted into the pericardium. Furthermore, it is also possible to lift the heart in the pericardium with a low force due to the buoyancy of the liquid in the pericardium, and thus the back wall of the heart can be more easily accessed.

The above-described invention may be provided with a flow-channel joining portion that combines a supplying channel for supplying the liquid to the pericardium and an expelling channel for expelling the liquid from the pericardium into a single flow channel.

By providing such a flow-channel joining portion, the supplying channel for supplying the liquid into the pericardium and the expelling channel for expelling the liquid from the pericardium can be connected together to the pipe at the body exterior. By doing so, the operation for feeding the liquid into the pericardium can be simplified by reducing the number of the liquid-feeding routes (for example, tubes).

In the above-described invention, a plurality of the pumps may be provided; and the supplying channel for supplying the liquid to the pericardium and the expelling channel for expelling the liquid from the pericardium may be connected to separate pumps.

By employing such a configuration, the supplying channel for supplying the liquid into the pericardium and the expelling channel for expelling the liquid from the pericardium can be provided as separate routes. By doing so, it is possible to maintain high clearness of the liquid in the pericardium by supplying fresh liquid to the pericardium from the supplying channel, and it is possible to obtain a clear image of the interior of the pericardium by means of an endoscope or the like.

The above-described invention may be provided with an electrocardiogram generating portion that generates an electrocardiogram from the electrocardiographic information detected by the electrocardiographic-information detecting portion; and an R-wave detecting portion that detects an R-wave from the electrocardiogram generated by the electrocardiogram generating portion, wherein the controlling portion causes the pump to operate after a predetermined period of time has elapsed since the time when the R-wave is detected by the R-wave detecting portion.

By employing such a configuration, periods of contraction and expansion of the heart can be ascertained accurately by detecting the R waves from the electrocardiogram by means of the R-wave detecting portion, and the liquid can be injected into and expelled from the pericardium by operating the pump in accordance with that timing. By doing so, cardiac tamponade can reliably be prevented.

In the above-described invention, the controlling portion may cause the pump to operate so that the amount of liquid supplied to the pericardium and the amount of liquid expelled from the pericardium become substantially equal.

By doing so, it is possible to keep the interior of the pericardium at a substantially constant pressure, and it is possible to reduce damage to the heart and the pericardial membrane due to pressure fluctuations of the liquid in the pericardium. In addition, because there is no increase or decrease in the amount of liquid in the pericardium between heart beats, the amount of liquid in the pericardium can stably be controlled for an extended period of time.

In the above-described invention, the controlling portion may control the pump so that a liquid-feeding speed is gradually increased when the liquid supply to the pericardium is started and the liquid-feeding speed is gradually decreased before the liquid supply to the pericardium ends.

By doing so, the liquid-supplying resistance can be reduced at the time of starting up the operation of the pump and shutting down the operation thereof, especially when switching between liquid supply and liquid discharge, and thus, accurate liquid-supply control is possible.

In the above-described invention, the controlling portion may control the pump so that a liquid-feeding speed is gradually increased when the liquid expelling from the pericardium is started and the liquid-feeding speed is gradually decreased before the liquid expelling from the pericardium ends.

By doing so, the liquid-discharging resistance can be reduced at the time of starting up the operation of the pump and shutting down the operation thereof, especially when switching between liquid supply and liquid discharge, and thus, accurate liquid-discharge control is possible.

In the above-described invention, the controlling portion may control the pump so that the amount of change in the liquid-feeding speed of the pump becomes constant.

By doing so, it is possible to eliminate an increase in the liquid-feeding resistance when the liquid-feeding speed abruptly changes, which makes it possible to reduce the burden on the pump and also to perform stable liquid-feeding control.

(Additional Item 1)
A pericardial-liquid level control method comprising:
inserting a pipe into the pericardium and detecting electrocardiographic information; and,
in synchronization with the detected electrocardiographic information, supplying liquid into the pericardium via the pipe during contraction of the heart and also expelling the liquid from the pericardium via the pipe during expansion of the heart.

(Additional Item 2)
A pericardial-liquid level control method according to Additional Item 1, wherein
an electrocardiogram is generated from the electrocardiographic information, and an R-wave is also detected from the electrocardiogram; and
the liquid is supplied into or expelled from the pericardium after a predetermined amount of time has elapsed since the time of the R-wave detection.

(Additional Item 3)
A pericardial-liquid level control method according to Additional Item 1, wherein the liquid is supplied to or expelled from the pericardium so that the amount of liquid supplied to the pericardium and the amount of liquid expelled from the pericardium become substantially equal.

(Additional Item 4)
A pericardial-liquid level control method according to Additional Item 1, wherein the liquid is supplied to the pericardium by gradually increasing the liquid-feeding speed when the liquid supply to the pericardium is started and by gradually decreasing the liquid-feeding speed before the liquid supply to the pericardium ends.

(Additional Item 5)
A pericardial-liquid level control method according to Additional Item 1, wherein the liquid is expelled from the pericardium by gradually increasing the liquid-feeding speed when the liquid expelling from the pericardium is started and by gradually decreasing the liquid-feeding speed before the liquid expelling from the pericardium ends.

(Additional Item 6)
A pericardial-liquid level control method according to Additional Item 4 or 5, wherein the liquid is supplied to or expelled from the pericardium so that the amount of change in the liquid-feeding speed for the pericardium is constant.

REFERENCE SIGNS LIST

A pericardial membrane
B heart
C pericardium
1, 2, 3 pump
5 pump control device (controlling portion)
6 electrocardiograph (electrocardiogram-generating portion)
7a, 7b electrocardiogram electrode (electrocardiographic-information detecting portion)
8 physiological-electrolyte-solution container
9 waste-liquid container
10 check-valve-equipped cock (flow-channel joining portion)
11 sheath (pipe)
12, 12a, 12b endoscope
13 liquid-feeding route
14 ultrasonic probe
15a, 15b check valve
21 R-wave detecting portion
22 operation-signal generating portion
30 connector (flow-channel joining portion)
101, 102, 103, pericardial-liquid level control system

The invention claimed is:

1. A pericardial-liquid level control system comprising:
   a pipe that is inserted into the pericardium;
   a pump that supplies liquid to the pipe and that expels liquid from the pipe;
   an electrocardiographic-information detecting portion that detects electrocardiographic information; and
   a controller that, in synchronization with the electrocardiographic information detected by the electrocardiographic-information detecting portion, controls the pump so that the liquid is supplied to the pericardium via the pipe during contraction of the heart and the liquid is expelled from the pericardium via the pipe during expansion of the heart, and
   a flow-channel joining portion that combines a supplying channel for supplying the liquid to the pericardium and an expelling channel for expelling the liquid from the pericardium into a single flow channel;
   wherein the controller further causes the pump to operate so that an amount of liquid supplied to the pericardium and an amount of liquid expelled from the pericardium become substantially equal.

2. The pericardial-liquid level control system according to claim 1, further comprising:
   an electrocardiogram generating portion that generates an electrocardiogram from the electrocardiographic information detected by the electrocardiographic-information detecting portion; and
   an R-wave detecting portion that detects an R-wave from the electrocardiogram generated by the electrocardiogram generating portion,
   wherein the controller causes the pump to operate after a predetermined period of time has elapsed since the time when the R-wave is detected by the R-wave detecting portion.

3. The pericardial-liquid level control system according to claim 1, wherein the controller controls the pump so that a liquid-feeding speed is gradually increased when the liquid supply to the pericardium is started and the liquid-feeding speed is gradually decreased before the liquid supply to the pericardium ends.

4. The pericardial-liquid level control system according to claim 1, wherein the controller controls the pump so that a liquid-feeding speed is gradually increased when the liquid expelling from the pericardium is started and the liquid-feeding speed is gradually decreased before the liquid expelling from the pericardium ends.

5. The pericardial-liquid level control system according to claim 3, wherein the controller controls the pump so that the amount of change in the liquid-feeding speed of the pump becomes constant.

6. The pericardial-liquid level control system according to claim 4, wherein the controller controls the pump so that the amount of change in the liquid-feeding speed of the pump becomes constant.

7. A pericardial-liquid level control system comprising:
   a pipe that is inserted into the pericardium;
   a pump that supplies liquid to the pipe and that expels liquid from the pipe;
   an electrocardiographic-information detecting portion that detects electrocardiographic information;
   a controller that, in synchronization with the electrocardiographic information detected by the electrocardiographic-information detecting portion, controls the pump so that the liquid is supplied to the pericardium via the pipe during contraction of the heart and the liquid is expelled from the pericardium via the pipe during expansion of the heart; and
   a flow-channel joining portion that combines a supplying channel for supplying the liquid to the pericardium and an expelling channel for expelling the liquid from the pericardium into a single flow channel.

* * * * *

UNITED STATES PATENT AND TRADEMARK OFFICE
CERTIFICATE OF CORRECTION

PATENT NO. : 9,662,446 B2  
APPLICATION NO. : 14/283288  
DATED : May 30, 2017  
INVENTOR(S) : Hiroshi Fukuda Page 1 of 1

It is certified that error appears in the above-identified patent and that said Letters Patent is hereby corrected as shown below:

On the Title Page

Insert:
--(30) Foreign Application Priority Data
Dec. 09, 2011   (JP).....................................2011-270259--

Signed and Sealed this
Twenty-first Day of November, 2017

Joseph Matal
*Performing the Functions and Duties of the
Under Secretary of Commerce for Intellectual Property and
Director of the United States Patent and Trademark Office*